(12) United States Patent
Anderson et al.

(10) Patent No.: US 8,722,579 B2
(45) Date of Patent: May 13, 2014

(54) BIOCIDAL COMPOSITION FOR TREATING WATER

(75) Inventors: Robert Ian Anderson, Mitcham (AU); Paul Seidl, Berwick (AU)

(73) Assignee: Waterco Limited, Rydalmere (AU)

( * ) Notice: Subject to any disclaimer, the term of this patent is extended or adjusted under 35 U.S.C. 154(b) by 0 days.

(21) Appl. No.: 13/984,717

(22) PCT Filed: Feb. 10, 2012

(86) PCT No.: PCT/AU2012/000121
§ 371 (c)(1),
(2), (4) Date: Aug. 27, 2013

(87) PCT Pub. No.: WO2012/106765
PCT Pub. Date: Aug. 16, 2012

(65) Prior Publication Data
US 2013/0331265 A1    Dec. 12, 2013

(30) Foreign Application Priority Data
Feb. 10, 2011    (AU) ................................ 2011900437

(51) Int. Cl.
*A01N 59/16*    (2006.01)
*A01N 25/30*    (2006.01)
*C02F 1/50*    (2006.01)
*C02F 1/52*    (2006.01)
*C02F 1/54*    (2006.01)
*C02F 1/56*    (2006.01)
*C02F 103/42*    (2006.01)

(52) U.S. Cl.
USPC ........ 504/152; 504/150; 504/158; 424/78.08; 424/78.09; 424/78.37; 424/78.38; 424/616; 210/755; 210/764

(58) Field of Classification Search
USPC ............ 504/150, 152, 158; 424/78.08, 78.09, 424/78.37, 78.38, 616; 210/755, 764
See application file for complete search history.

(56) References Cited

U.S. PATENT DOCUMENTS

| | | | | |
|---|---|---|---|---|
| 4,319,020 A | * | 3/1982 | Coscia et al. | 528/405 |
| 5,683,953 A | * | 11/1997 | Mills | 502/405 |
| 6,312,604 B1 | | 11/2001 | Denkewicz, Jr. et al. | |
| 7,030,163 B2 | | 4/2006 | Duneas | |
| 7,384,573 B2 | | 6/2008 | Brummett | |
| 7,758,752 B2 | | 7/2010 | Pan et al. | |
| 2003/0156981 A1 | | 8/2003 | Mills | |

FOREIGN PATENT DOCUMENTS

WO          94/29266 A1    12/1994

OTHER PUBLICATIONS

Chemical Book entry for Poly(dimethylamine-co-epichlorohydrin). Datasheet [online]. [Retrieved on Feb. 22, 2014]. Retrieved from the Internet: <URL: http://www.chemicalbook.com/ChemicalProductProperty_EN_CB2157269.htm>.*
Guidechem entry for CAS No. 25988-97-0. Datasheet [online]. [Retrieved on Feb. 22, 2014]. Retrieved from the Internet: <URL: http://www.guidechem.com/cas-259/25988-97-0.html>.*
International Search Report issued in corresponding application No. PCT/AU2012/000121 mailed Mar. 7, 2012.

* cited by examiner

*Primary Examiner* — John Pak
(74) *Attorney, Agent, or Firm* — Carter, DeLuca, Farrell & Schmidt LLP

(57) ABSTRACT

An aqueous composition for treatment of water comprising: (a) an N,N-dimethyl-2-hydroxypropylammonium chloride polymer; (b) lanthanum chloride; and (c) a dimethylamine epichlorohydrin ethylenediamine polymer; and a method of treating water using the composition.

27 Claims, No Drawings

BIOCIDAL COMPOSITION FOR TREATING WATER

FIELD

The present invention relates to a composition for the treatment of water to control algal growth by reducing the concentration of phosphate and flocculating suspended solids. The invention also relates to a method of preparing such a composition, and to methods for its use.

The materials and methods of the invention may be used to reduce phosphate levels and control algal growth in water in a range of situations, but are particularly applicable to the maintenance of water in swimming pools, spas, hot tubs, and the like where algal growth may pose a health hazard to humans.

BACKGROUND

Water in swimming pools, spas and hot tubs is constantly re-circulated. Although this water is usually filtered continuously to keep it free of suspended matter, it frequently contains algae, phosphate and dissolved solids. Regular sanitising will control the bacteria in the water; however, the water needs to be maintained in a fashion to remove the food sources and breeding grounds for algae.

The proliferation of algal growth in water is facilitated by the presence of phosphates. Phosphates are present in most water sources and there is a significant buildup of phosphates from plant material and from waste products of people using the water for recreation. Thus, a need arises for a way to remove these phosphates and the associated growth of algae.

In maintaining a swimming pool, spa or hot tub, traditionally the owner is required to undertake a series of tests. This can be done by taking a water sample to a professional chemical supplier and relying on the professional to diagnose the problem. The problem can lead to the need to use excessive amounts of chemical products to eliminate a chain reaction of problem sources. Usually, the steps taken to treat water to remove or inhibit algae includes analysis of the water and several (generally three or four) treatments of phosphate remover over a period of a week or more.

The phosphate which supports algal growth generally needs to be removed to acceptable levels before an algicide is effective in reducing or eliminating algae. Following the use of an algicide a flocculating agent may be used, generally after a period of a couple of days, to remove particulates including matter remaining from treatment of algae.

Generally, the process requires consultation of a pool specialist or chemical supplier and is time consuming for the untrained general public. Also, it is difficult to achieve effective results due to the number of steps and different chemicals required which lead to poor compliance with the required steps often necessitating further intervention of a specialist or chemical supplier and expense for the owner. Poor control of algae produces serious health risks.

Contaminated water can sometimes also require treatment with chemicals in high dosages, known as shock treatment. Shock treatment is not always successful, and dumping of the water is sometimes necessary when such a treatment is used.

Numerous chemical compounds have been reported for use in swimming pools, spas and hot tubs.

Quaternary ammonium compounds have been reported as being useful in swimming pools, spas, and hot tubs as algaecides.

The quaternary ammonium compounds used as algicides have required relatively high levels to be effective or have required prolonged contact times. However, at such high concentration levels, quaternary ammonium salts in general have the potential of producing objectionable, aesthetically unpleasing turbid swimming pool water having a high total organic carbon content. Such high concentrations of quaternary ammonium salts may also increase the likelihood of skin irritation of people using those bathing facilities.

Popular sanitisers used in swimming pools, spas and hot tubs include chlorine and/or bromine. These are effective bactericides, but suffer from a number of disadvantages. One such disadvantage is that these disinfectants may cause eye irritation. In addition to this, a growing number of people have become allergic to chlorine and/or bromine. Such allergies include skin allergies to chlorine and/or bromine. Further, asthmatics can be irritated by the presence of chlorine. Chlorine residues also pose environmental concerns. Therefore, a water treatment product which is suitable for use in chlorine and bromine free water is sometimes required.

U.S. Pat. No. 7,030,163 describes a biocidal composition which includes, poly(hexamethylene)biguanide, didecyldimethylammonium chloride a homogenizing agent and a flocculating agent. The composition is used to treat water to control microorganisms.

WO 1994/29266 describes a sanitizer composition characterized by a bactericidal effective amount of the combination of (a) a quaternary ammonium compound selected from the group consisting of (hydrogenated tallow) 2-ethylhexyl dimethyl ammonium salt, dicoco dimethyl ammonium salt, and mixtures thereof; and (b) a copper (II) ion source.

US 2003/0156981 describes tablet and granules for treatment of pool water comprising at least one water-soluble sanitizer selected from chlorinating or brominating agents, chlorinated hydantoins, chlorinated isocyanurates, chlorinated glycourils and oxazolidinones and at least one lanthanide compound (other than phosphate) compacted or otherwise formed into a physically coherent body. A matrix, carrier or binder is adapted to dissolve and/or disintegrate over time in pool water may also be used. The sanitizer and lanthanide are dispersed within the tablet or granule so that, upon dissolution or disintegration of the tablet or granule, the lanthanide compound will be released. A method involves placing the tablet or granules in the flow of water to the pool filter so that, as the tablet or granule dissolves, the sanitizer is dissolved into the pool water and the lanthanide is carried into the filter where it is retained as a particulate solid that is effective in removing phosphate from pool water circulating in the filter and from whence it can be removed by backwashing.

The need for a simplified method of treating and maintaining water is apparent.

The applicants have discovered that compositions which incorporate a specific polyquaternary amine algicide with a specific quaternary ammonium flocculating compound and a lanthanum salt derivative provides a single stable composition able to treat contaminated water and inhibit build-up of phosphates, bio film and algae.

The discussion of the background to the invention herein is included to explain the context of the invention. This is not to be taken as an admission that any of the material referred to was published, known or part of the common general knowledge as at the priority date of any of the claims.

SUMMARY OF THE INVENTION

The present invention relates to an aqueous composition for the treatment of water comprising, (a) an N,N-dimethyl-2-hydroxypropylammonium chloride polymer; (b) a water soluble lanthanide, preferably lanthanum chloride; and (c) a dimethylamine epichlorohydrin ethylenediamine polymer.

In some embodiments of the invention, the weight ratio of the dimethylamine epichlorohydrin ethylenediamine polymer to the N,N-dimethyl-2-hydroxypropylammonium chloride polymer is in the range of 1:6 to 4:1, preferably about 1:4 to about 4:1, preferably wherein the weight ratio of the dimethylamine epichlorohydrin ethylenediamine polymer to the N,N-dimethyl-2-hydroxypropylammonium chloride polymer is about 1:1 to 1:3 and most preferably about 1:2. In some embodiments, the weight ratio of the dimethylamine epichlorohydrin ethylenediamine polymer to the lanthanide (preferably lanthanum chloride) is in the range of about 1:4 to about 2.5:1, preferably wherein the weight ratio of the dimethylamine epichlorohydrin ethylenediamine polymer to the lanthanide is in the range of about 1:4 to 1:1 and most preferably is about 1:2.

The composition may further comprise an antifoam agent. The antifoam agent may be a water soluble silicone emulsion. In some particular embodiments the antifoam is selected from the group of siloxanes, such as dimethyl siloxanes and mixtures thereof. The antifoam in one set of embodiments is present in an amount of from 0.01% w/w to 1% w/w of the composition.

The composition further comprises water. The water may be present in an amount of about 50% w/w to about 95% w/w, preferably about 60% w/w to about 95% w/w of the composition and more preferably from 70% w/w to 90% w/w of the composition. In some specific cases the water may be present in an amount of about 85% w/w of the composition. In another embodiment the water is present in an amount in the range of from 60% w/w to 80% w/w. The dimethylamine epichlorohydrin ethylenediamine polymer may be present in the range of about 1% w/w to about 8% w/w, preferably about 2% w/w to about 6% w/w of the composition. In some cases the dimethylamine epichlorohydrin ethylenediamine polymer is present in an amount of about 3% w/w of the composition. In some embodiments the N,N-dimethyl-2-hydroxypropylammonium chloride polymer is present in an amount 4% w/w to about 10% w/w, preferably about of about 4% w/w to about 8% w/w of the composition, and in some specific cases the N,N-dimethyl-2-hydroxypropylammonium chloride polymer is present in an amount of about 6% w/w of the composition. In some embodiments the lanthanide (preferably lanthanum chloride) is present in an amount of about 4% w/w to about 8% w/w of the composition, and in some cases the lanthanide is present in an amount of about 6% w/w of the composition (based on the weight of the lanthanum compound, In the case of lanthanum chloride and hydrates thereof the weight is based on $LaCl_3$).

In some embodiments of the composition, the composition contains no chlorinating or brominating agents.

The invention also relates to a composition consisting essentially of: (a) an N,N-dimethyl-2-hydroxypropylammonium chloride polymer; (b) a water soluble lanthanide, preferably lanthanum chloride; (c) a dimethylamine epichlorohydrin ethylenediamine polymer, (d) water; and (e) optionally antifoam.

The invention also relates to a method of making an aqueous solution for treatment of water, the method comprising combining the components in aqueous composition In one embodiment the steps comprise: (a) combining water and an N,N-dimethyl-2-hydroxypropylammonium chloride polymer and mixing until a homogenous solution is formed; (b) subsequently combining a water soluble lanthanide to the solution and mixing until homogenous; (c) subsequently combining a dimethylamine epichlorohydrin ethylenediamine polymer to the solution and mixing until homogenous to form the aqueous solution.

In an alternative embodiment the method comprises the following steps in sequence:
(a) forming a homogenous mixture of dimethylamine epichlorohydrin ethylenediamine polymer and at least part of the water;
(b) combining the homogenous mixture with N,N-dimethyl-2-hydroxypropyl ammonium chloride; and
(c) combining the mixture with water soluble lanthanide, preferably lanthanum chloride.

The components may be used in the form of commercially available aqueous concentrates.

In some embodiments of the method the dimethylamine epichlorohydrin ethylenediamine polymer is present in the range of about 2% w/w to about 6% w/w of the aqueous solution, and in some specific embodiments the dimethylamine epichlorohydrin ethylenediamine polymer is present in an amount of about 3% w/w of the aqueous solution. The N,N-dimethyl-2-hydroxypropylammonium chloride polymer may be present in an amount of about 4% w/w to about 8% w/w of the aqueous solution, and in some embodiments may be present in an amount of about 6% w/w of the aqueous solution. The lanthanide, preferably lanthanum chloride, may be present in an amount of about 4% w/w to about 8% w/w of the aqueous solution, and in some specific embodiments may be present in an amount of about 6% w/w of the aqueous solution. The water may be present in an amount of about 50% w/w to 95% w/w, preferably about 60% w/w to about 90% w/w and still more preferably about 70% w/w to about 90% w/w of the aqueous solution, and in some specific embodiments is present in an amount of about 85% w/w of the aqueous solution.

In some embodiments of the method, the mixing is carried out at a temperature in the range of about 10° C. to about 25° C., preferably the mixing is carried out at 15° C.

In some embodiments the method comprises combining an antifoam agent to the solution and mixing until homogenous. The antifoam agent may be selected from the group consisting of siloxanes, silicone dimethyl and mixtures thereof. In some embodiments the antifoam agent is present in an amount of about 0.05% w/w to about 0.15% w/w of the aqueous solution, and in some specific embodiments the antifoam agent is present in an amount of about 0.1% w/w of the aqueous solution.

In some embodiments of the method the aqueous solution contains no chlorinating or brominating agents.

The invention also relates to a method consisting essentially of: (a) combining water and an N,N-dimethyl-2-hydroxypropylammonium chloride polymer and mixing until a homogenous solution is formed; (b) subsequently combining a water soluble lanthanide to the solution and mixing until homogenous; (c) subsequently combining a dimethylamine epichlorohydrin ethylenediamine polymer to the solution and mixing until homogenous to form the aqueous solution.

The invention also relates to an aqueous solution for the treatment of water made by a method as hereinbefore described.

The invention further relates to a method of treating water comprising applying to the water a composition as hereinbefore described. The composition may be in the form of an aqueous solution. The amount of the aqueous composition applied to the water may be in the range of from about 10 ml to 200 ml per 1,000 L water and preferably 50 ml and 150 ml per 1,000 L of water to be treated. In some specific embodiments the amount of the aqueous composition applied to the water is about 50 ml per 1,000 L of water to be treated. The composition is preferably applied as a single dose. About 50 ml to 100 ml of the aqueous composition may be applied to the water no more frequently than once per week or less often such as no more than once per fortnight, depending on the frequency of usage of the water and the amount of contamination. Typically for spas the single dose need be applied no more than once per fortnight and in the case of pools no more than once per month.

Throughout the description and the claims of this specification the word "comprise" and variations of the word such as "comprising" and "comprises" is not intended to exclude other additions, components, integers or steps.

DETAILED DESCRIPTION OF THE INVENTION

The dimethylamine epichlorohydrin ethylenediamine polymer (CAS No. 42751-79-1) is a polyquaternary amine which acts as a flocculating agent. The compound is available from Cytec Australia Holdings Pty Ltd under the trade name Superfloc® C-573 Flocculant. It is available as a polyquaternary amine in water as 48-52% w/w.

The N,N-dimethyl-2-hydroxypropylammonium chloride polymer, a polyquat, is a quaternary ammonium compound which acts as a control for algae and bacteria. The compound is available from Lonza Ltd under the trade name Barquat PQ-2, with 49-51% w/w active ingredient.

The lanthanide, such as lanthanum chloride, acts as a phosphate remover. Lanthanum chloride (CAS No. 10025-84-0) is available from Redox Pty Ltd under the product name Lanthanum Chloride 60% min w/w.

The antifoam may be any water soluble silicone emulsion. A suitable antifoam agent is a siloxanes such as polydimethyl siloxane (CAS No. 63148-62-9).

We have found that compositions containing a dimethylamine epichlorohydrin ethylenediamine polymer, a N,N-dimethyl-2-hydroxypropylammonium chloride polymer and lanthanum chloride provide a stable composition. When present in an aqueous solution, no precipitation occurs on long term storage.

We have found the composition of the invention to provide significant synergy when compared with the individual components. Treatment of water with the composition required approximately one quarter of the recommended dose of each chemical if used individually to achieve a low level of phosphate, such as less than 0.5 ppm and preferably less than 0.2 from water (even in a 20,000 liter or more pool) with a single dose.

There is thus further provided in one set of embodiments a method of treating water comprising applying to the water an aqueous composition as hereinbefore described.

In one set of embodiments the aqueous composition is applied to water to be treated at a dose rate in the range of from 10 ml to 200 ml of composition per 1000 L of water. Preferably the dose rate is no more than 150 ml, such as no more than 50 ml, per 1000 L of water to be treated. The composition used in such doses may comprise:
 (a) the N,N-dimethyl-2-hydroxypropylammonium chloride polymer is present in an amount of from 4% w/w to 10% w/w, preferably 4% w/w to 8% w/w, of the composition;
 (b) the water soluble lanthanide, preferably lanthanum chloride, is present in an amount of from 2% w/w to 8% w/w, preferably 4% w/w to 8% w/w, of the composition;
 (c) the dimethylamine epichlorohydrin ethylenediamine polymer is present in an amount in the range of from 1% w/w to 8% w/w, preferably 2% w/w to 6% w/w of the composition; and
 (d) the water is present in an amount of from 50% w/w to 95% w/w, preferably 70% w/w to 90% w/w, of the composition.

In one set of embodiments the composition is added to water to be treated at a dose rate to provide water soluble lanthanide, lanthanum chloride, in an amount in the range of no more than 200 g, preferably no more than 100 g and most preferably no more than 80 g in 20,000 liters of water to be treated.

In one set of embodiments the composition is added to water to be treated at a dose rate to provide a concentration of dimethylamine epichlorohydrin ethylenediamine polymer of no more than 100 g per 20,000 L, preferably no more than 50 g per 20,000 L and most preferably, no more than 30 g per 20,000 L.

In one set of embodiments the composition is added to water at a dose rate to provide:
 (a) A water soluble lanthanide, lanthanum chloride, concentration in the range of from 20 g to 100 g per 20,000 L; and
 (b) N,N-dimethyl-2-hydroxypropylammonium chloride polymer concentration in the range of from 10 to 80 g per 20,000 L.

In one set of embodiments the composition is added to water to be treated at a dose rate to provide:
 (a) water soluble lanthanide, preferably lanthanum chloride, concentration in the range of from 20 to 100 g per 20,000 L; and
 (b) dimethylamine epichlorohydrin ethylenediamine polymer concentration in the range of from 10 to 100 g per 20,000 L.

In one set of embodiments the composition is added to water to be treated at a dose rate to provide:
 (a) N,N-dimethyl-2-hydroxypropylammonium chloride polymer concentration in the range of from 10 g to 80 g per 20,000 L; and
 (b) Dimethylamine epichlorohydrin ethylenediamine polymer concentration in the range of from 10 g to 100 g per 20,000 L.

In one set of embodiments the composition is added to water to be treated at a dose rate to provide:
 (a) water soluble lanthanide, lanthanum chloride concentration in the range of from 20 g to 100 g per 20,000 L;
 (b) N,N-dimethyl-2-hydroxypropylammonium chloride polymer concentration in the range of from 10 g to 80 g per 20,000 L; and
 (c) dimethylamine epichlorohydrin ethylenediamine polymer concentration in the range of from 10 g to 100 g per 20,000 L.

It is particularly preferred and an advantage of the invention that maintenance of low levels of phosphate may be maintained by dosing the composition, preferably in a single dose, no more frequently than once a fortnight, for example, no more than once a fortnight for spas and no more than once a month for pools, although more frequent dosing may be used if desired. In the case of pools the dosing regimen may be no more than once per month and for spas, no more than once per fortnight. While the above dose rates are single doses in other embodiments they may be applied in, for example, no more than three doses of the cumulative amounts specified over a period of a six weeks for spas and 12 weeks for pools.

The composition according to the invention can be used to treat water in swimming pools, spas, hot tubs and the like. It can be used to treat such water which is contaminated, or may be used to maintain the ideal conditions of the water.

Sanitizers suitable for pre-treatment of the water to be treated with the composition include any registered sanitizers, and specifically include chlorine, bromine, and hydrogen peroxide including stabilized hydrogen peroxide and hydrogen peroxide with silver compounds. Generally, hydrogen peroxide is preferred. The water to be treated in accordance with the invention will preferably have a pH less than 7.6 and more preferably has a pH in the range of from 6.8 to 7.4. The total alkalinity of the water to be treated in accordance with the invention is preferably in the range of less than 80 ppm and more preferably in the range of from 60 ppm to 80 ppm.

The composition can also be used in water which is free from chlorine and/or bromine. Thus the composition can be used in swimming pools, spas and hot tubs which are free from chlorine and/or bromine, and are therefore suitable for use by those who suffer from chlorine and/or bromine allergies and also asthmatics.

The composition and method of the invention allow effective algae control with a single treatment to reduce phosphate nutritional source, reducing or controlling existing algae infestation if any and removing particulate debris including that derived from control of algae. The composition allows a surprising level of phosphate reduction and control of algae and maintenance of a pool, spa or hot tub in a state clear and free of algal infestation with an all in one low dose of chemicals which provides control and maintenance in a condition clear of algae generally for weeks before further treatment is needed. The composition and method significantly reduce the complexities and chemical handling involved in phosphate level reduction and algae control and provides a synergy which allows the required levels of chemicals to reduce to as much as one quarter of that usually required.

Examples of materials and methods for use with the compositions and methods of the present invention will now be provided. In providing these examples, it is to be understood that the specific nature of the following description is not to limit the generality of the above description.

EXAMPLES

Example 1

Preparation of the Composition

In order to prepare the composition, 739.9 kg of water was placed in a mixing tank, and the mixer was started. 120 kg of a solution containing 50% w/w N,N-dimethyl-2-hydroxypropylammonium chloride polymer was added into the mixing tank and the solution mixed until homogenous. 100 kg of a solution containing 60% w/w lanthanum chloride was then added to the mixing tank, and the solution mixed until homogenous. 160 kg of a solution containing 25% w/w dimethylamine epichlorohydrin ethylenediamine polymer was then added to the mixing tank, and the solution mixed until homogenous.

Example 2

Preparation of the Composition

In order to prepare the composition, 739.9 kg of water was placed in a mixing tank, and the mixer was started. 120 kg of a solution containing 50% w/w N,N-dimethyl-2-hydroxypropylammonium chloride polymer was added into the mixing tank and the solution mixed until homogenous. 100 kg of a solution containing 60% w/w lanthanum chloride was then added to the mixing tank, and the solution mixed until homogenous. 160 kg of a solution containing 25% w/w dimethylamine epichlorohydrin ethylenediamine polymer was then added to the mixing tank, and the solution mixed until homogenous. 1.0 kg of a solution containing 95% w/w siloxane antifoam agent was added to the mixer and mixed until homogenous.

Example 3

Method of Using the Composition

The following example relates to the treatment of water in a spa, however a similar process would be applicable to the treatment of water in swimming pools and hot tubs.

A spa having a capacity of 1,400 liters was dosed with 70 ml of the composition of Example 1. The water was allowed to circulate through the filter, and after 35 minutes. The concentration of phosphate and presence of algae was monitored. The concentration of phosphate and the presence of algae was prevented. The process, to prevent the build-up of bio film, algae, inhibit phosphate concentration and remove flocculated debris took approximately 35 minutes and required the application of one solution to the water.

In order to maintain ideal conditions of the water in the spa, 50 ml of the composition of Example 1 was added to the spa initially. It was found that a regular fortnightly maintenance dose of 50 ml per 1000L of water eliminated the need for "shock" treatment of the water. The composition was also found to reduce the demand for sanitizers as it maintained the water in cleaner state after use.

Example 4

Method of Using the Composition

A spa having a capacity of 1,400 liters was dosed with 70 ml of the composition of Example 2, and the water was allowed to circulate through the filter for 35 minutes. The concentration of phosphorus, and presence of algae was monitored, and the same results as discussed in Example 3 were obtained. In addition, no excessive foaming took place.

Comparative Example A

The following is a typical process applied for treating water not of the invention. The following example relates to the treatment of water in a spa, however, a similar process would be applicable to the treatment of water in swimming pools and hot tubs.

A spa having a capacity of 1,500 liters was dosed with 500 ml of a 15% active phosphate remover lanthanum chloride to treat contamination of 0.5 ppm of phosphate. This treatment was repeated three times (i.e. 4 doses). The spa was required to circulate through filter for 60 minutes. The spa was then dosed with 70 grams of a copper based algaecide to treat malodour and turbidity of the water. The spa was required to circulate with filters removed for 4.5 hours to allow the algaecide contact time with the surface of the spa including the blowers. The spa was then dosed with 50 ml of a 25% active flocculent and allowed to circulate with the filters in place for 1 hour. The spa water was tested for pH and alkalinity. The results indicated that the water was required to be adjusted by the use of an alkalinity increaser to 120 ppm and the pH reduced from 8.2 to 7.4 in small increments of approximately 30 grams over approximately 6 hours. This time was required to allow the reaction between the base and the acid to stabilise and avoid a pH bounce.

The concentration of phosphate, and presence of algae was monitored. Phosphate was reduced by 50% and required continuous treatment with further doses of phosphate remover. Monitoring showed that the malodour and turbidity were removed.

The process to prevent the build-up of bio film, algae, inhibit phosphate concentration and remove flocculants took approximately 11.5 hours and required the application of five different processes to the water.

The composition of Examples 1 and 2 provided a mixture of chemicals able to prevent the build-up of bio film, algae and reduce the phosphate concentration and remove by means of flocculation suspended solids.

The composition was also able to be used in a method to treat water, by providing as a single measured dose containing three chemicals usually needed to rescue water. The composition of Examples 1 and 2 were found to be a stable solution.

Contaminated water usually requires treatment in high dosages of chemicals, known as shock treatment. Shock treatment is not always successful, and dumping of the water is sometimes necessary when such a treatment is used. However, it was found that the properties of the composition of Examples 1 and 2 inhibited the build-up of contamination and reduced the need for shock treatment. The composition was also found to be compatible with many types of sanitizers (not only $H_2O_2$) used in the treatment of swimming pools, spas and hot tubs.

As is shown in the contrast between Examples 3 and 4, and Comparative Example 5, the application of the composition of Examples 1 and 2 saved over five hours when compared to the process of Comparative Example 5. The process therefore saved costs associated with the dosing and application of four different processes to the water, compared with the application of one composition in Examples 3 and 4.

The composition of Examples 1 and 2 was also found to be compatible for use in swimming pools, spas and hot tubs which are chlorine and bromine free. The use of the compositions can therefore be kind to asthmatics, gentle on sensitive skin and not harmful to the environment.

The composition eliminated and prevented the establishment of phosphate build up, algae growth resulting from that build up or the build-up of total dissolved solids.

The composition of Examples 1 and 2 was found to be stable in conditions of 4° C. to 50° C. It was also found to be fast acting and readily miscible in water. It was also compatible with hydrogen peroxide, and calcium chloride as used in standard swimming pool, spa and hot tub treatment. Further, it was found to be non-hazardous and the composition on dilution was found to be safe to dump on gardens, and in sewage and septic systems. The composition was also found to work efficiently in both hard and soft water.

Examples 5 and 6 and Comparative Examples B and C

These Examples compare the composition (Example 5) and method (Example 6) of the invention with a conventional system (Comparative Example B) used to control algae and phosphate and a control (Comparative Example C) in which the components used in the composition of the invention are dosed separately.

Preparation of Pool

A 20,000 liter above-ground pool was dosed with trisodium phosphate (TSP to bring the phosphate levels to 1.5 ppm. A standard pool configuration (for above ground pools is 350 lt/min pump C75 cartridge filter) was used and the pool was observed until presence of algae was first visually evident. The pool had a pH of about 7 and total alkalinity of about 60.

Comparative Example B (CE-B)

Use of Convention Maintenance Method

A pool prepared as above was treated according to the following protocol:

On day 1, a 500 ml quantity of a 150 g/L solution of lanthanum chloride in water (available from pool and spa stores in Australia under the Aquapure brand) was dosed to the pool and after 24 hours the phosphate level was found to be 0.75 ppm. On day 3, another 500 ml dose of the same lanthanum chloride solution was added to the pool, and after 24 hours, the phosphate level was found to be greater than 0.2 ppm. On day 5 another 500 ml dose of the same lanthanum chloride solution was added to the pool, and after 24 hours the phosphate level was found to be greater than 0.2 ppm. On day 7 a further 500 ml lanthanum chloride solution was added to the pool, and after 24 hours the phosphate level was found to be less than 0.2 ppm. On day 9, 1200 ml of an algicide (150 g/L benzalkonium chloride, available from pool stores in Australia under the "Aquapure" brand) was added to the phosphate-depleted pool, and allowed to act for 48 hours. On day 11, a 500 g quantity of flocculant (aluminium sulphate, available from pool stores in Australia under the "Aquapure" brand) was added to the pool and allowed to act for 10 days. The use of the above protocol led to the creation of a phosphate-depleted pool of good clarity.

Comparative Example C (CE-C)

Control Experiment with Key Components

On day 1, a 500 ml quantity of a 150 g/L solution of lanthanum chloride in water (available from pool & spa stores in Australia under the "Aquapure" brand) was dosed to the pool and after 24 hours the phosphate level was found to be 0.75 ppm. On day 3, another 500 ml dose of the same lanthanum chloride solution was added to the pool, and after 24 hours, the phosphate level was found to be greater than 0.2 ppm. On day 5 another 500 ml dose of the same lanthanum chloride solution was added to the pool, and after 24 hours the phosphate level was found to be greater than 0.2 ppm. On day 7 a further 500 ml lanthanum chloride solution was added to the pool, and after 24 hours, the phosphate level was found to be less than 0.2 ppm. On day 9, a dose of 400 mls of an algicide (Lonza Barquat PQ2 comprising a 50% aqueous solution of N,Ndimethyl-2-hydroxypropylammonium chloride polymer, CAS*25988-97-0) was added to the phosphate-depleted pool, and allowed to act for 48 hours. On day 11, a 600 ml quantity of flocculant (CYTEC C573 comprising 25% liquid polyquaternary amine in water, specifically comprising dimethylamine epichlorohydrinethylenediamine polymer CAS #42751-79-1) was added to the pool and allowed to act for 10 days. The use of the above protocol led to the creation of a phosphate-depleted pool of good clarity.

Example 5

Formulation According to the Invention 310 parts water was added to an agitated tank followed by 60 parts CYTEC C573. After 10 minutes of agitation, 60 parts Lonza Barquat PQ2 was added. After a further 10 minutes of agitation, 50 parts of a solution of 600 g/L lanthanum chloride in water was added. After a further 10 minutes of agitation, 0.5 parts of a silicone antifoam (Price Chemicals in NSW, Australia CAS #63148-62-9) was added with further mixing. Per liter of formulation, the components were as shown in Table 1.

TABLE 1

Example 5 Composition

| Component | Composition | Parts of composition in F21 | Percentage of composition solids |
|---|---|---|---|
| water | | 659 | |
| Floc Cytec C573 dimethylamine epichlorohydrinethylenediamine | 25% solids in water | 120 | 3% |
| Biocide Barquat PQ2 N,Ndimethyl-2-hydroxypropylammonium chloride polymer, | 50% solids in water | 120 | 6% |
| Lanthanum Chloride | 60% solids in water | 100 | 6% |
| Antifoam | emulsion | 1 | |
| | | 1000 | |

Example 6 (Ex-6)

Pool Treatment Protocol Using Composition of Example 5

A pool prepared as described in Example 5 was treated by addition of 1 liter of composition of Example 5. After 24 hours the level of phosphates was found to be less than 0.2 ppm, and after 72 hours, the pool water had good clarity.

The benefits associated with the use of the formulation of the invention are shown in Table 2 with respect to steps required operator time and quantity of respective chemicals.

TABLE 2

| Parameter | Control method (CE - B) | Method of the invention (Ex - 6) | Comments |
|---|---|---|---|
| Number of steps | 10 | 1 | Dosing and measuring counted as separate steps |
| Time of entire treatment | 20 days | 3 days | Includes waiting for treatment to take effect |
| Operator time required for treatment | 5.25 hrs | 0.25 hrs | 0.25 hrs for dosing |
| Quantity of lanthanum chloride (solid) | 300 g (4 dosing steps) | 60 g (1 dosing step) | Cumulative over dosing steps |
| Quantity of quat Biocide (as 50% solution) | 400 mls | 120 mls | |
| Quantity of floc (as 25% solution) | 600 mls | 120 mls | |

As demonstrated in the Table 2 above the composition of the invention reduces significantly the operator time and chemicals required to achieve algae control and good clarity. While in the conventional and control protocols incremental additions of significant amounts of chemicals were required to achieve acceptable phosphate levels, the composition of the invention achieved suitable levels with a single addition. These levels were maintained over a long period (over four weeks) without further addition. Approximately a quarter of the amount of each of the chemicals was required using the composition of the invention to achieve acceptable levels of phosphate and good clarity when compared with use of the same chemicals individually.

It will be appreciated that various modifications and variations of the methods and compositions of the invention described herein will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are apparent to those skilled in the art are intended to be within the scope of the present invention.

The invention claimed is:

1. An aqueous composition for treatment of water comprising:
    (a) an N,N-dimethyl-2-hydroxypropylammonium chloride polymer;
    (b) a water soluble lanthanide; and
    (c) a dimethylamine epichlorohydrin ethylenediamine polymer.

2. The composition of claim 1, wherein the weight ratio of the dimethylamine epichlorohydrin ethylenediamine polymer to the N,N-dimethyl-2-hydroxypropylammonium chloride polymer is in the range of about 0.5:2 to about 2:0.5.

3. The composition of claim 1, wherein the weight ratio of the dimethylamine epichlorohydrin ethylenediamine polymer to the lanthanide is in the range of from about 1:4 to about 2.5:1.

4. The composition of claim 1, wherein the composition further comprises water in the range of from 50% w/w to 95% w/w.

5. The composition of claim 4, wherein the water is present in an amount of about 70% w/w to about 90% w/w of the composition.

6. The composition of claim 1, wherein the dimethylamine epichlorohydrin ethylenediamine polymer is present in an amount in the range of from 1% w/w to 8% w/w of the composition.

7. The composition of claim 1, wherein the N,N-dimethyl-2-hydroxypropylammonium chloride polymer is present in an amount of about 4% w/w to about 10% w/w of the composition.

8. The composition of claim 1, wherein the water soluble lanthanide is lanthanum chloride present in an amount of about 2% w/w to about 8% w/w of the composition.

9. The composition of claim 1, wherein:
    (a) the N,N-dimethyl-2-hydroxypropylammonium chloride polymer is present in an amount of from 4% w/w to 8% w/w of the composition;
    (b) lanthanum chloride is present in an amount of from 4% w/w to 8% w/w of the composition;
    (c) the dimethylamine epichlorohydrin ethylenediamine polymer is present in an amount in the range of from 2% w/w to 6% w/w of the composition; and
    (d) the water is present in an amount of from 70% w/w to 90% w/w of the composition.

10. The composition of claim 1, wherein the composition further comprises an antifoam agent in an amount in the range of from 0.01% w/w to 1% w/w of the composition.

11. The composition of claim 1, wherein the composition is essentially free of chlorinating or brominating agents.

12. The composition of claim 1, consisting essentially of
   (a) an N,N-dimethyl-2-hydroxypropylammonium chloride polymer;
   (b) lanthanum chloride;
   (c) a dimethylamine epichlorohydrin ethylenediamine polymer;
   (d) water; and
   (e) optionally antifoam.

13. The composition of claim 1, wherein the water soluble lanthanide is lanthanum chloride.

14. A method of treating water comprising applying to the water the composition of claim 1.

15. The method of claim 14, wherein the composition is applied to the water (i) no more than once per week, (ii) no more than once per fortnight for spas, or (iii) no more than once per month for pools.

16. A method according to claim 14, wherein the composition is applied to water at a dose rate in the range of from 10 ml to 200 ml of composition per 1000 L of water.

17. A method according to claim 14, wherein the composition is added to water to be treated at a dose rate to provide lanthanum chloride in an amount in the range of no more than 200 g in 20,000 liters of water to be treated.

18. A method according to claim 14, wherein the water to be treated has been pre-treated with a sanitizing agent.

19. A method according to claim 14, wherein the composition is added to water to be treated at a dose rate to provide a concentration of N,N-dimethyl-2-hydroxypropylammonium chloride polymer of no more than 100 g per 20,000 L.

20. A method according to claim 14, wherein the composition is added to water to be treated at a dose rate to provide a concentration of dimethylamine epichlorohydrin ethylenediamine polymer of no more than 100 g per 20,000 L.

21. A method according to claim 14, wherein the composition is added to water to be treated at a dose rate to provide:
   (a) a lanthanum chloride concentration in the range of from 20 g to 100 g per 20,000 L; and
   (b) N,N-dimethyl-2-hydroxypropylammonium chloride polymer concentration in the range of from 10 to 80 g per 20,000 L.

22. A method according to claim 14, wherein the composition is added to water at a dose rate to provide:
   (a) Lanthanum chloride concentration in the range of from 20 to 100 g per 20,000 L; and
   (b) Dimethylamine epichlorohydrin ethylenediamine polymer concentration in the range of from 10 to 100 g per 20,000 L.

23. A method according to claim 14, wherein the composition is added to water to be treated at a dose rate to provide:
   (a) N,N-dimethyl-2-hydroxypropylammonium chloride polymer concentration in the range of from 10 g to 80 g per 20,000 L; and
   (b) Dimethylamine epichlorohydrin ethylenediamine polymer concentration in the range of from 10 g to 100 g per 20,000 L.

24. A method according to claim 14, wherein the composition is added to water to be treated at a dose rate to provide:
   (a) Lanthanum chloride concentration in the range of from 20 g to 100 g per 20,000 L;
   (b) N,N-dimethyl-2-hydroxypropylammonium chloride polymer concentration in the range of from 10 g to 80 g per 20,000 L; and the range of from 10 g to 80 g per 20,000 L; and
   (c) Dimethylamine epichlorohydrin ethylenediamine polymer concentration in the range of from 10 g to 100 g per 20,000 L.

25. A method according to claim 16, where the composition is applied to the water to be treated (i) no more than once per week, (ii) no more than once per fortnight for spas, or (iii) no more than once per month for pools.

26. A method according to claim 14, wherein the water to be treated is a swimming pool or spa.

27. A method according to claim 18, wherein the sanitizing agent is hydrogen peroxide.

* * * * *